(12) United States Patent
Fransson et al.

(10) Patent No.: US 8,395,384 B2
(45) Date of Patent: Mar. 12, 2013

(54) SIMULTANEOUS RELAXATION TIME INVERSION

(75) Inventors: Carl-Magnus Fransson, Cleveland, TX (US); Carla B. Hara Fransson, legal representative, Cleveland, TX (US); Ronald E. Cherry, Humble, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 519 days.

(21) Appl. No.: 12/519,956

(22) PCT Filed: Jan. 18, 2007
(Under 37 CFR 1.47)

(86) PCT No.: PCT/US2007/001416
§ 371 (c)(1),
(2), (4) Date: Aug. 10, 2010

(87) PCT Pub. No.: WO2008/088335
PCT Pub. Date: Jul. 24, 2008

(65) Prior Publication Data
US 2011/0025324 A1    Feb. 3, 2011

(51) Int. Cl.
*G01V 3/00* (2006.01)
(52) U.S. Cl. .................................. 324/303; 324/300
(58) Field of Classification Search .................. 324/300, 324/301, 302, 306, 307, 3–9, 314; 702/8
See application file for complete search history.

(56) References Cited

U.S. PATENT DOCUMENTS

| | | |
|---|---|---|
| 4,278,892 A | 7/1981 | Baatz et al. |
| 4,743,854 A | 5/1988 | Vinegar et al. |
| 5,023,551 A | 6/1991 | Kleinberg et al. |
| 5,596,274 A | 1/1997 | Sezginer |
| 6,512,371 B2 | 1/2003 | Prammer |
| 6,545,471 B2 | 4/2003 | Wollin |
| 6,856,132 B2 * | 2/2005 | Appel et al. .................. 324/303 |
| 7,176,682 B2 * | 2/2007 | Galford et al. ............... 324/303 |
| 2003/0214286 A1 | 11/2003 | Heidler |
| 2004/0196038 A1 | 10/2004 | Kruspe et al. |
| 2005/0030021 A1 | 2/2005 | Prammer et al. |
| 2006/0055403 A1 | 3/2006 | Freedman |
| 2006/0132131 A1 | 6/2006 | Fleury et al. |
| 2006/0290350 A1 | 12/2006 | Hursan et al. |
| 2010/0277167 A1 * | 11/2010 | Romero ....................... 324/303 |

(Continued)

FOREIGN PATENT DOCUMENTS

| | | |
|---|---|---|
| AU | 2007343899 | 1/2012 |
| WO | WO-2005/036208 A2 | 4/2005 |

OTHER PUBLICATIONS

"Australian Application Serial No. 2007343899, Examiner Report mailed Jun. 1, 2011", 3 pgs.

(Continued)

*Primary Examiner* — Brij Shrivastav
(74) *Attorney, Agent, or Firm* — Schwegman Lundberg & Woessner, P.A.; Alan Bryson

(57) ABSTRACT

In some embodiments, apparatus and systems, as well as methods, may operate to acquire fluid signature data representing a plurality of nuclear magnetic resonance echo trains associated with fluids in a material, to simultaneously invert a plurality of relaxation time models to provide inverted results, and to determine fluid properties using the inverted results. The relaxation time models may be associated with the fluids using the fluid signature data after constraining ratios of $T_1$ relaxation times to $T_2$ relaxation times.

41 Claims, 9 Drawing Sheets

U.S. PATENT DOCUMENTS

2012/0035851 A1* 2/2012 Romero .............................. 702/8

OTHER PUBLICATIONS

"Australian Application Serial No, 2007343899, Response filed Aug. 25, 2011 to Office Action mailed Jun. 1, 2011", 3 pgs.

"Indonesian Application U.S. Appl. No. W-00200902291, Response filed Jun. 1, 2011 to Office Action dated Mar. 3, 2011", (w/ English Translation), 12 pgs.

Sun, B., et al., "A global inversion method for multi-dimensional NMR logging", *J Magn Reson.*, 172(1), (Jan. 2005), 152-60.

"International Application Serial No. PCT/US2007/001416, International Preliminary Report on Patentability mailed May 1, 2012", 4 pgs.

"Australian Application Serial No. 2007343899, Response mailed May 4, 2011 to Examiner Report mailed Dec. 15, 2010", 2 pgs.

"Indonesian Application Serial No. W-00200902291, Office Action mailed Mar. 14, 2011", 2 pgs.

"Argentina Application Serial No. 080100210, Office Action mailed Oct. 20, 2009", 5 pgs.

"Argentina Application Serial No. 080100210, Response filed Jan. 4, 2010 to Office Action mailed Oct. 20, 2009", 14 pgs.

"International Application Serial No. PCT/US2007/01416, International Search Report mailed Mar. 31, 2008", 2 pgs.

"International Application Serial No. PCT/US2007/01416, Response filed Jun. 30, 2008 to Written Opinion mailed Mar. 31, 2008", 3 pgs.

"International Application Serial No. PCT/US2007/01416, Written Opinion mailed Mar. 31, 2008", 8 pgs.

"Australian Application Serial No. 2007343899, First Examiner Report mailed Aug. 23, 2010", 6 pgs.

"Austrialian Application Serial No. 2007343899, Response filed Nov. 30, 2010 to Examiner's Report dated Aug. 23, 2010", 3 pgs.

"Australian Application Serial No. 2007343899, Subsequent Examiner Report mailed Dec. 15, 2010", 3 Pgs.

Fang, S., et al., "Quantification of Hydrocarbon Saturation in Carbonate Formations Using Simultaneous Inversion of Multiple NMR Echo Trains", (SPE 90569), *SPE Annual Technical Conference and Exhibition*, Houston, Texas, (Sep. 2004), 26-29.

Loren, J. D, et al., "Relations Between Pore Size Fluid and Matrix Properties, and NML Measurements", *SPE Journal*, vol. 10(3), (1970), 268-278.

\* cited by examiner

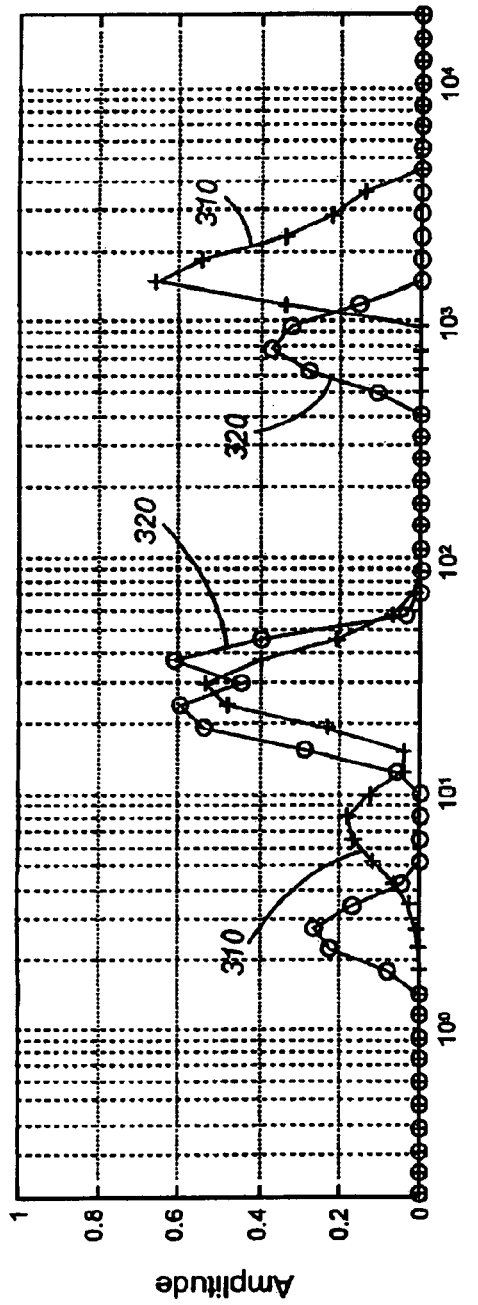
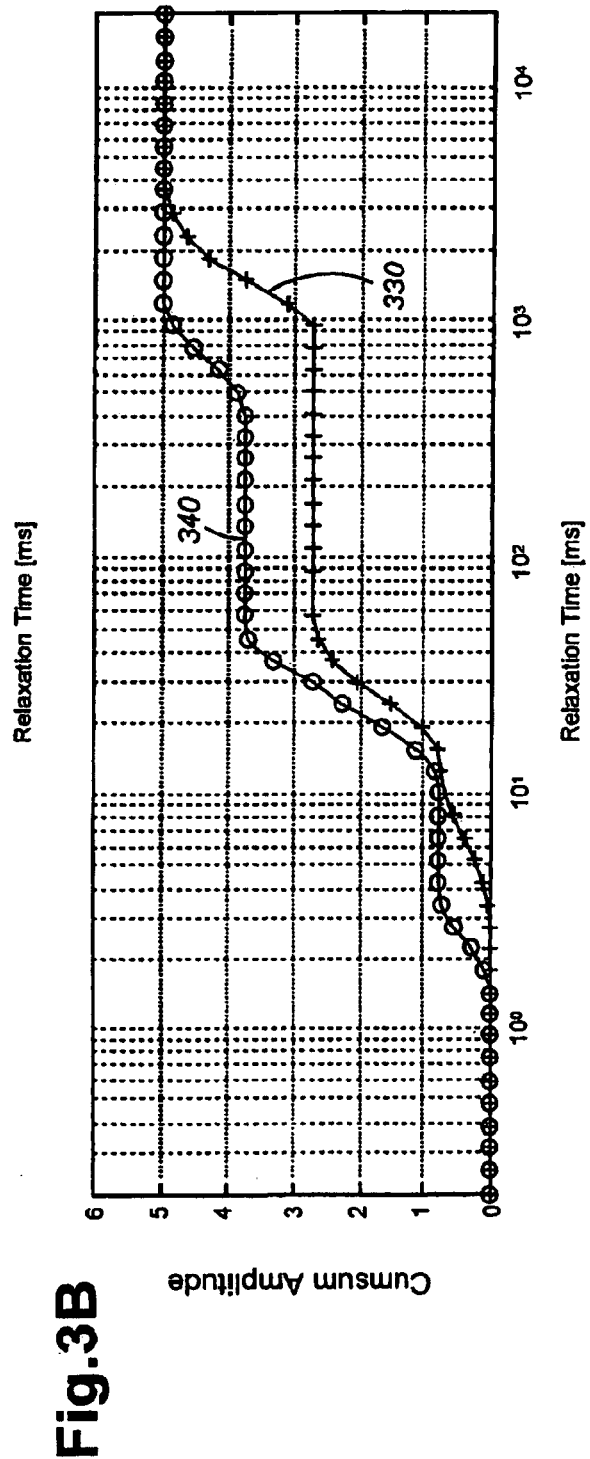
Fig.3A
Fig.3B

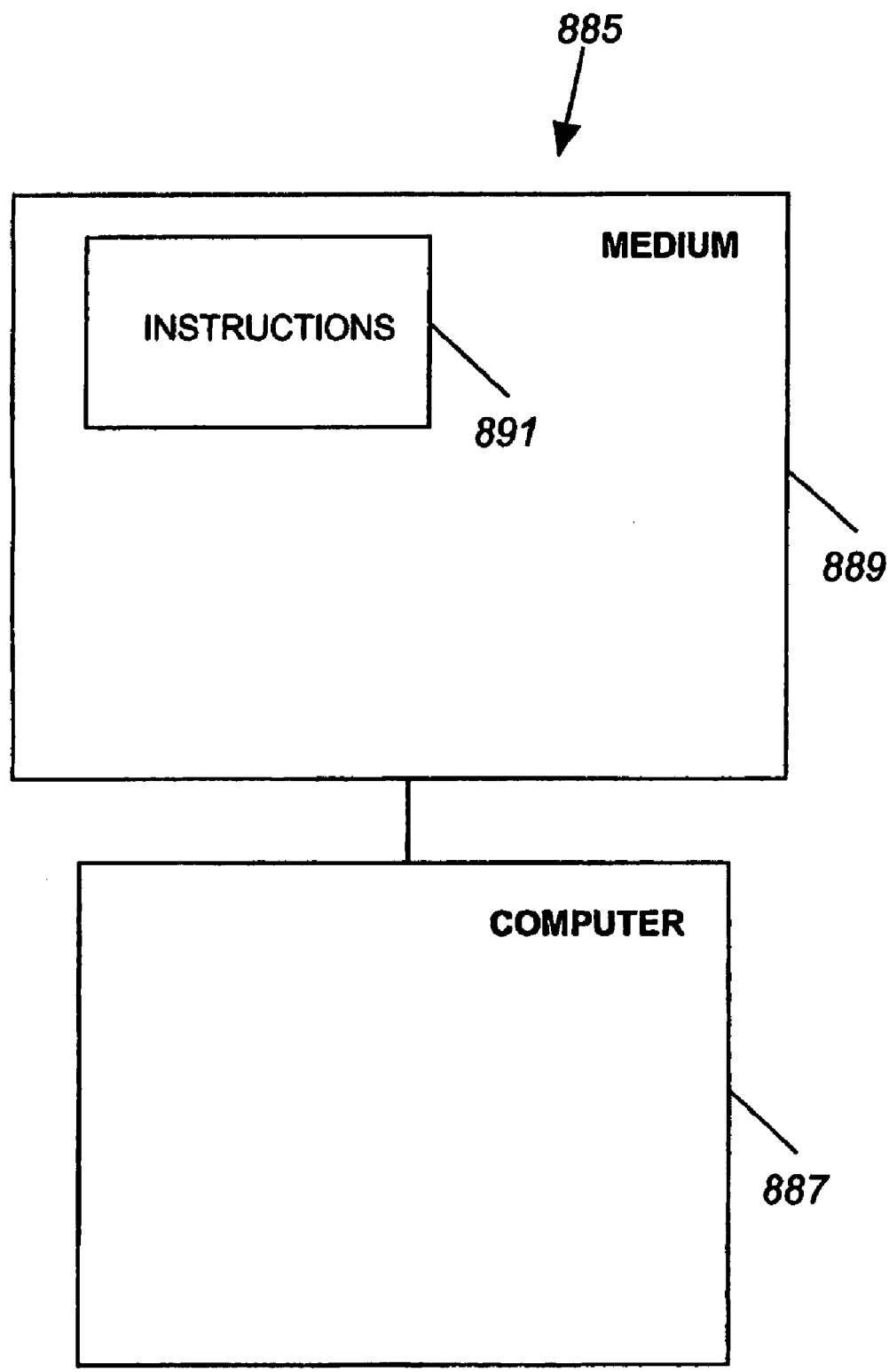

SIMULTANEOUS RELAXATION TIME INVERSION

This application is a U.S. National Stage Filing under 35 U.S.C. 371 from International Patent Application Serial No. PCT/US2007/001416, filed Jan. 18, 2007, and published on Jul. 24, 2008 as WO 2008/088335, the contents of which are incorporated herein by reference in their entirety.

RELATED APPLICATIONS

This disclosure is related to PCT Application Serial No. PCT/US2006/021973, titled "Fluid Typing", filed on Jun. 6, 2006, and PCT Application Serial No. PCT/US2006/028621, titled "Fluid Saturation Estimation", filed on Jul. 21, 2006, both assigned to the assignee of the embodiments disclosed herein, Halliburton Energy Services, Inc. and incorporated herein by reference in their entirety.

TECHNICAL FIELD

Various embodiments described herein relate to the characterization of different types of matter, including apparatus, systems, and methods used to determine fluid properties.

BACKGROUND INFORMATION

Fluids (e.g., oil, water, gas) exist in a variety of materials, including geological formations. It is often useful to determine the properties of a fluid, or of multiple fluids, such as viscosity, diffusivity, and fluid type. Fluid identification models based on nuclear magnetic resonance (NMR) use NMR measurements to acquire fluid signature data from a selected material in the form of echo trains containing information about relaxation times, which in turn can be used to identify fluids and determine fluid properties. Interested readers may refer to U.S. Pat. No. 6,512,371 (incorporated herein by reference in its entirety) describing how NMR data can be acquired.

To determine fluid properties, echo trains can be used to estimate NMR $T_1$ and $T_2$ relaxation time distributions. Unfortunately, total porosity values derived separately from $T_1$ and $T_2$ relaxation time distributions may not agree, giving rise to interpretation uncertainties with respect to the fluid type data.

BRIEF DESCRIPTION OF THE DRAWINGS

FIGS. 3A and 3B illustrate separate and cumulative $T_1$ and $T_2$ distributions, respectively, according to various embodiments of the invention.

FIG. 8 is a block diagram of an article according to various embodiments of the invention.

DETAILED DESCRIPTION

Figure 1:
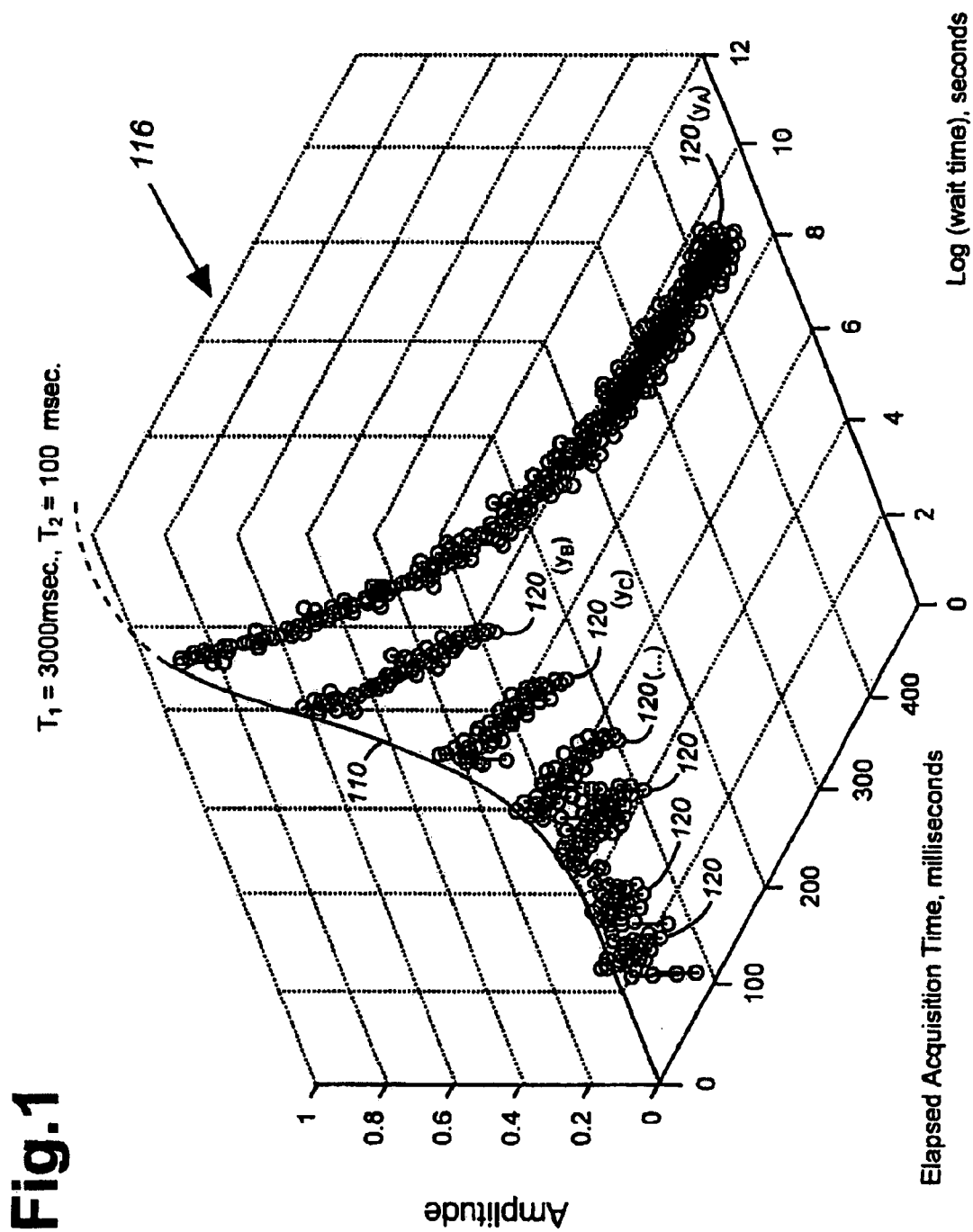
FIG. 1 illustrates an NMR $T_1$ measurement comprising several NMR $T_2$ measurements along a $T_1$ buildup curve according to various embodiments of the invention.

In some embodiments of the invention, the challenges described above may be addressed by using nuclear magnetic resonance (NMR) measurements to acquire fluid signature data from a selected material (e.g., a geological formation) in the form of echo train information. Thereafter, a variety of approaches to solve for porosity measurements may be used. One may be called Two-Dimensional Fluid Characterization, or "2DFC", and another may be called Dual Spectra Analysis, or "DSA".

In 2DFC, both $T_1$ and $T_2$ relaxation time distributions may be determined at the same time, or substantially simultaneously. The coincidence of $T_1$ and $T_2$ data in a two-dimensional plane permits developing an image of porosity information that is relatively easy to interpret because the location of various fluid types is often readily apparent. While no assumption regarding the polarization of the fluid may be needed, the time used to find a solution may be longer than is desired. The data processing time needed depends on many factors, including: (1) the number of echoes acquired; (2) the signal to noise ratio of the acquired data; (3) the fluid types and volumes involved; and (4) the desired resolution in the two-dimensional $T_1$ and $T_2$ space.

In DSA, the solution method is substantially sequential, since simultaneous $T_1$-$T_2$ inversion occurs after a time-zero inversion. While the benefit of finding a solution more quickly may accrue, this occurs at the expense of assuming that the fluid is fully polarized. In addition, no image of porosity is available; only the relative distributions of individual $T_1$ and $T_2$ relaxation data, and the distribution of porosity at each point is unknown. Further sampling at various locations may be needed to confirm interpretation of the data. Finally, error can accumulate, due to estimates used in the early part of the solution process.

For the purposes of this document, a "fluid" is any material that has an NMR transverse relaxation time constant (i.e., $T_2$) of greater than 1 millisecond, and the variables used herein are defined as follows:

D=self-diffusion coefficient [cm²/s]
G=tool-dependent magnetic field gradient [G/cm]
i=index for the sequence number [unitless]
j=index for the echo number [unitless]
$K_0$=matrix of models associated with acquired echo train data [unitless]
$K_{0A}$=$K_0$ associated with acquired echo train data $y_A$ [unitless]
$K_1$=discrete longitudinal relaxation time kernel [unitless]
$K_2$=discrete transverse relaxation time kernel [unitless]
$K_{2A}$=$K_2$ associated with acquired echo train data $y_A$ [unitless]
$L_x$=regularization matrix [unitless]
M=Matrix of acquired echo trains for one sequence [unitless]
m=total number of echoes in the $T_1$ $T_2$ measurement
$m_A$=number of echoes in the echo train of the longest wait time [unitless]
m=vector of time-zero echo amplitudes [unitless]
$n_E$=number of acquired echoes for each wait time [unitless]
$n_{tw}$=number of wait times used in the acquisition [unitless]
$n_1$=number of discretized values in a $T_1$ relaxation distribution [unitless]
$n_2$=number of discretized values in a $T_2$ relaxation distribution [unitless]
P=$T_1$ polarization matrix [unitless]
t=measurement time [ms]
S=pore surface area [μm²]
$T_1$=longitudinal relaxation time [ms]
$T_{1B}$=$T_1$ bulk [ms]
$T_{1S}$=$T_1$ surface [ms]

$T_2$=transverse relaxation time [ms]
$T_{2B}$=$T_2$ bulk [ms]
$T_{2D}$=$T_2$ diffusion [ms]
$T_{2S}$=$T_2$ surface [ms]
$t_E$=time between echoes (i.e., echo spacing time) along an echo train [ms]
$t_w$=wait time [ms]
$t_{wa}$=wait time associated with acquired echo train data $y_A$ [ms]
V=fluid volume in a pore [$\mu m^3$]
X=discrete two-dimensional probability density function [p.u.]
x=vectorized version of X [p.u.]
$x_{T1}$=$T_1$ distribution in DSA method
$x_{T2A}$=$T_2$ distribution in DSA method corresponding to echo train data $y_A$ [p.u.]
Y=matrix of measured echoes [p.u.]
y=vector of acquired echo train data [p.u.]
$y_A$=acquired echo train data for longest wait time [p.u.]
$\alpha_x$=regularization parameter [unitless]
$\kappa_1$=continuous diffusion kernel [unitless]
$\kappa_2$=continuous relaxation kernel [unitless]
$\rho$=surface relativity of the wetting phase [$\mu m/ms$]
$\gamma=2\pi 4258$=proton gyromagnetic ratio [Hz/G]

FIG. 1 illustrates an NMR $T_1$ measurement, comprising several NMR $T_2$ measurements along a $T_1$ buildup curve 110 according to various embodiments of the invention. In this measurement context, a data sequence 116 can be defined as one NMR $T_1$ measurement, comprising $n_{tw}$ wait times $t_W$ resulting in different polarization levels on the $T_1$ buildup curve 110. After each wait time $t_W$, $n_E$ echoes may be acquired with an echo spacing of $t_E$, resulting in an echo train 120. In some embodiments of the invention, each of these echo trains 120 ($y_A$, $y_B$, $y_C$, etc.) can be used to retrieve the echoes on the $T_1$ buildup curve 110 (e.g., time-zero echoes) via standard linear $T_2$ inversion procedures.

For purposes of spatial economy, the process of linear inversion will not be discussed in detail, as it is well known to those of ordinary skill in the art. However, readers that desire to learn more about how $T_2$ distributions can be estimated from a single echo train (e.g., as a standard least-squares problem) may consult "NMR Pore Size Distributions and Permeability at the Well Site" by Prammer, SPE paper 28368, 69th Annual Technical Conference and Exhibition, New Orleans, La., 1994; "Practical Optimization," by Gill et al., Academic Press, London and New York (1981); and the "User's guide for LSSOL (version 1.0): A Fortran package for Constrained Linear Least-Squares and Convex Quadratic Programming," by Gill et al., Technical Report SOL 86-1, Systems Optimization Laboratory, Dept. of Operations Research, Stanford University, 1986.

To ensure that total porosity and $T_2$ fluid components are resolved accurately via a single $T_2$ measurement, a long echo train (e.g., a thousand or more echoes) using a long wait time (e.g., about 10-20 seconds) is useful. This is because a valid $T_2$ measurement requires full polarization prior to data acquisition. In fact, some fluids, such as bulk water, may use a wait time of 60 seconds or more to reach full polarization. Resolving $T_1$ fluid components makes use of echo trains corresponding to multiple wait times whose echo trains may be significantly shorter (e.g. on the order of ten echoes) than the echo train needed to fully resolve $T_2$ components. This is because the $T_1$ fluid components can be derived from information about the $T_1$ build-up curve 110. Increasing the length of the echo trains may result in improved accuracy for time-zero intercepts on the $T_1$ buildup curve 110, and consequently improve the accuracy of the $T_1$ fluid components.

In some cases, a sufficiently accurate determination of total porosity and $T_1$ fluid components does not require the fluid to be fully polarized, reducing the need for extremely long wait times. When both $T_1$ and $T_2$ fluid components are desired, echo trains at multiple wait times are needed. However, the data series having the longest wait time does not need to be as long, since echo trains for shorter wait times carry some of the $T_2$ information, resulting in relaxed requirements in the longest wait time. In addition, the longest wait time does not need to be as long if physical relationships between the $T_1$ and $T_2$ components are taken into account when resolving the fluid components. This will be discussed in more detail below.

Acquiring such echo train data is applicable to both the 2DFC and the DSA methods. $T_1$ spectrum data may be provided by a formation tester, such as the Reservoir Description Tool (RDT™), available from the Halliburton Company's Energy Services Group, using a downhole NMR fluid analysis tool, including the integrated MRILab® service provided by Halliburton Energy Services. Samples can be taken and saved in a downhole tool sample chamber (e.g., a Halliburton Reservoir Description Tool (RDT™) sample chamber). A data set including a plurality of NMR echo trains may also be acquired using a magnetic resonance imaging log (MRIL) tool, similar to or identical to the formation evaluation and NMR logging tool models MRIL-Prime, MRIL-XL, and MRIL-WD developed by NUMAR Corporation of Exton, Pa.

To characterize fluids using the 2DFC method, one may begin by denoting M as the measured data, with subscripts A, B, C, . . . etc. corresponding to the $n_{tw}$ different echo trains, in decreasing order of wait time, such that $M_A(t)$ corresponds to the echo train of the longest wait time. In many of the various disclosed embodiments, one may also assume that total porosity in the $T_1$ and $T_2$ distributions are substantially identical.

The measured data for a particular wait time $M_A(t)$ may be related to the two-dimensional probability density function $f(T_1,T_2)$ by a Fredholm integral of the first kind:

$$M_A(t) = \iint \kappa_2(t,T_2) \cdot f(T_1,T_2) \cdot f_1(T_1) dT_1 dT_2, \quad (1)$$

where $\kappa_2 = e^{-t/T_2}$, and $\kappa_1 = 1 - e^{-t_{wA}/T_1}$.

To simplify the problem, the unknown parameters $T_1$ and $T_2$ may be discretized into $n_1$ and $n_2$ values, respectively, so that the only unknowns in equation (1) are the components in the function $f(T_1,T_2)$. Thus, in matrix notation, the discretized version of equation (1) can be written as:

$$y_A = K_{2A} X^T K_1^T \quad (2)$$

where $y_A \in \Re^{m_A \times 1}$, $K_{2A} \in \Re^{m_A \times n_2}$, $X \in \Re^{n_1 \times n_2}$, $K_1 \in \Re^{1 \times n_1}$, and $m_A$ denotes the number of echoes in each echo train. In an optimization framework, the problem to determine X can then be posed as:

$$X^* = \arg\min_{X \geq 0} \| Y_A - K_{2A} X^T K_1^T \|_F^2. \quad (3)$$

By lexicographically ordering the matrices X and Y into vectors, equation (3) may be reduced to a one-dimensional problem of the following vectorized form, where "*" indicates a mathematically optimal solution:

$$x^* = \arg\min_{x \geq 0} \| K_{0A} x - y_A \|_2^2, \quad (4)$$

where $K_{0A} \in \Re^{m_A \times n_1 n_2} = K_1 \otimes K_{2A}$, $x \in \Re^{n_1 n_2 \times 1}$, and $y_A \in \Re^{m_A \times 1}$. The remaining wait times can be incorporated into this framework by forming the following optimization problem:

$$x^* = \arg\min_{x \geq 0} \left\| \begin{bmatrix} K_{0A} \\ K_{0B} \\ K_{0C} \\ \ldots \end{bmatrix} x - \begin{bmatrix} y_A \\ y_B \\ y_C \\ \ldots \end{bmatrix} \right\|_2^2 \Leftrightarrow x^* = \arg\min_{x \geq 0} \|K_0 x - y\|_2^2, \quad (5)$$

where $K_0 \in \Re^{m \times n_1 n_2}$, $y \in \Re^{m \times 1}$, and m denotes the total number of echoes in a $T_1 T_2$ measurement. The matrices $K_1$ and $K_2$ are rank-deficient, so that solving equation (5) is an ill-conditioned problem. To provide a meaningful solution, regularization (smoothing) terms may be added to equation (5) as follows:

$$x^* = \arg\min_{x \geq 0} \|K_0 x - y\|_2^2 + \alpha_x \|L_x x\|_2^2, \quad (6)$$

where $\alpha_x$ is a regularization parameter determining the smoothness of the solution and $L_x \in \Re^{m \times n_1 n_2}$ is a regularization matrix.

In addition to regularizing (smoothing) the solution vector x, equation (6) can be extended to include explicit regularization terms for the $T_1$ and $T_2$ distributions by adding additional terms which include regularization parameters $\alpha_{T_2}$ and $\alpha_{T_1}$, as well as regularization matrices $L_{T_2}$ and $L_{T_1}$, which have all been preselected. This activity may be expressed by the following equation:

$$x^* = \arg\min_{x \geq 0} \|K_0 x - y\|_2^2 + \alpha_x \|L_x x\|_2^2 + \alpha_{T_2} \|L_{T_2} x\|_2^2 + \alpha_{T_1} \|L_{T_1} x\|_2^2. \quad (7)$$

Equation (7), the solution of which can be seen as a graph of porosity distribution in FIG. 4, discussed below, may be solved in a standard least-squares fashion, but may be computationally intensive and use significant amounts of memory. For example, solving equation (7) with m=1000, p=7; $n_1$=50, and $n_2$=50 can require an hour of time using a standard laptop computer. To more efficiently and robustly solve equation (7), the magnitude of the problem can be reduced by noting that parts of the two-dimensional $T_1$-$T_2$ space are infeasible. The attribute that may be used to define the infeasible regions in the two-dimensional $T_1$-$T_2$ space is the R distribution, where $R = T_1/T_2$ (i.e., R denotes the ratio $T_1/T_2$).

To study R, it is helpful to note the following well known relationships for $T_1$ and $T_2$ relaxation times:

$$\frac{1}{T_1} = \frac{1}{T_{1B}} + \frac{1}{T_{1S}}; \quad (8)$$

$$\frac{1}{T_2} = \frac{1}{T_{2B}} + \frac{1}{T_{2S}} + \frac{1}{T_{2D}}, \quad (9)$$

where subscripts B, S, and D stand for bulk, surface, and diffusion, respectively. In addition, we have:

$$\frac{1}{T_{1S}} = \rho_1 \frac{S}{V}; \quad (10)$$

$$\frac{1}{T_{2S}} = \rho_2 \frac{S}{V}; \text{ and} \quad (11)$$

$$\frac{1}{T_{2D}} = \frac{D(\gamma G t_E)^2}{12}; \quad (12)$$

where $\rho$32 surface relativity of the wetting phase (fluid proximate to the rock in the formation, assumed to be water), S=pore surface area, V=fluid volume in the pore, D=self diffusion coefficient, $\gamma$=proton gyromagnetic ratio, and G=magnetic field gradient. Equations (8)-(12) can be combined to form R as follows:

$$R = \frac{T_{1B}}{T_{2B}} \cdot \frac{\frac{1}{S/V}(T_{2D} + T_{2B}) + \rho_2 T_{2B} T_{2D}}{\frac{1}{S/V} T_{2D} + \rho_1 T_{1B} T_{2D}}. \quad (13)$$

It can now be seen that for large pores (e.g., no rock present)

$$\lim_{S/V \to 0} R = \frac{T_{1B}}{T_{2B}} + \frac{T_{1B}}{T_{2D}}, \quad (14)$$

and for small pores $$\lim_{S/V \to \infty} R = \frac{\rho_2}{\rho_1}. \quad (15)$$

Thus, in large pores (as may be the case for data from a downhole fluid analyzer, such as MRILab), R is affected mainly by diffusion, whereas in small pores, R may be controlled by a ratio of surface relaxivities. In prior inversion methods, R was assumed to be a scalar number, but it is important to realize that R as described herein is in fact a distribution.

The R distribution for water may be unimodal (e.g., having a single peak) in bulk fluids. However, due to the presence of both irreducible water (e.g., water that can not be produced from a formation) and free water in various formations, surface relaxivity may broaden the R distribution. For example, using the MRIL-Prime tool, the R of water may range from about 1 to 30 within the operating temperature range, whereas for the MRIL-XL tool, the R of water may vary from about 1 to 7. The difference in R between the two tools arises because the diffusion effect is tool-dependent (see equation (12) and the gradient G).

For the non-wetting phase (e.g., fluid that is not proximate to the rock in the formation), surface relaxation may be ignored so that R is primarily controlled by diffusion. Due to a high self-diffusivity, gas has a high R value, typically on the order of about 50 or higher when using the MRIL-Prime tool, and about 10 or higher when using the MRIL-XL tool. Due to a broad range of viscosity, the R value of oil may have the same range as that of bulk water, although the R distribution of oils may not be unimodal—depending on the composition of the oil. Given this information, it is easily seen that when a mixture of irreducible water and free fluid are present in a geological formation, the R distribution may be very broad, with multiple peaks. Taken together, these factors indicate that the R values described above can be used to avoid solving equation (7) for infeasible regions of the $T_1$-$T_2$ space.

Figure 2:
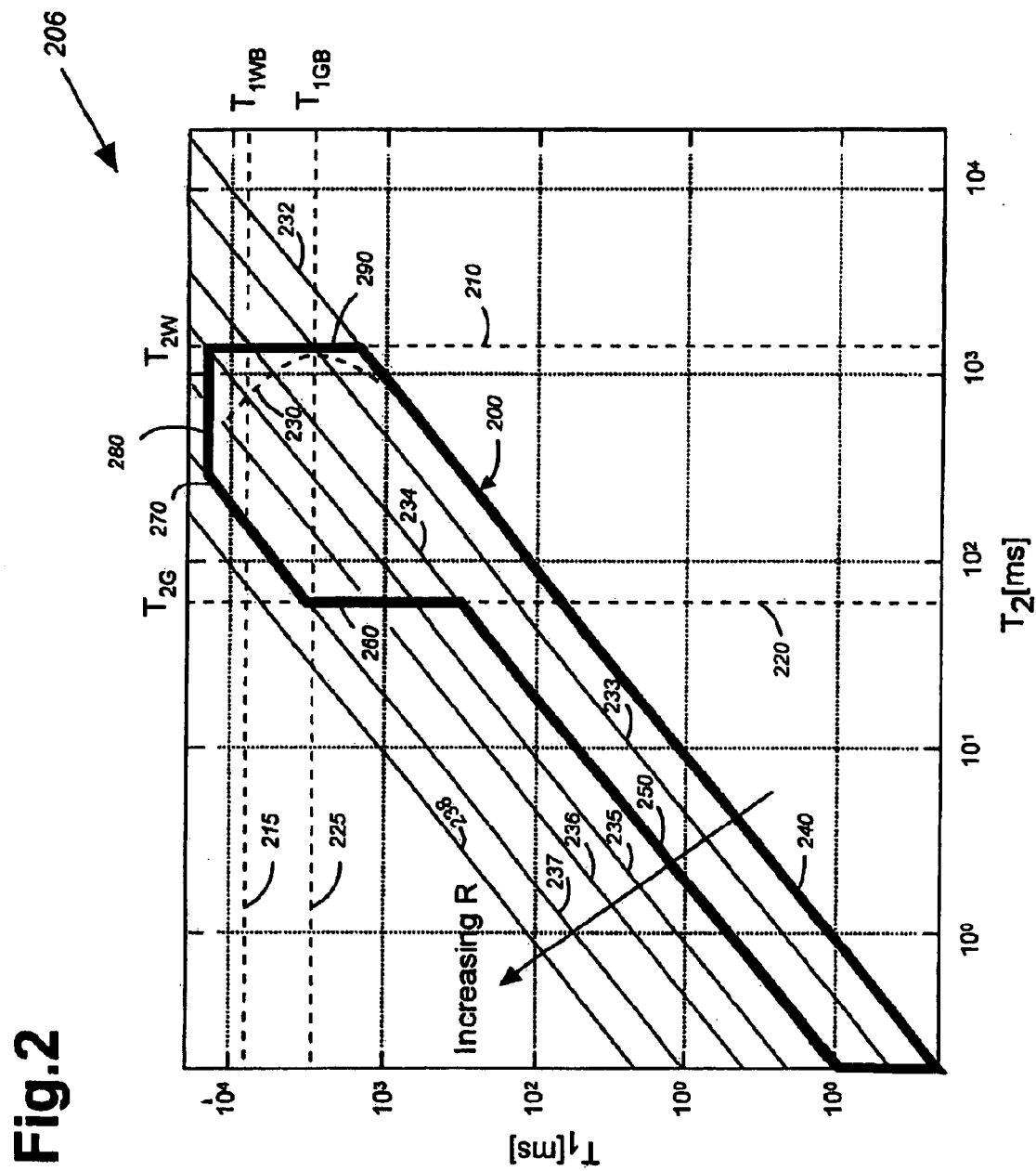
FIG. 2 illustrates the feasible boundary of a two-dimensional volumetric porosity solution space according to various embodiments of the invention.

FIG. 2 illustrates the feasible boundary 200 of a two-dimensional volumetric porosity solution space 206 according to various embodiments of the invention. The figure documents the use of an MRIL-Prime tool, with $t_E=0.9$, and assumed reservoir conditions of 90 C and 3000 psi. Values for $T_2$ and $T_{1B}$ for water ($T_{2W}$ 210 and $T_{1WB}$ 215) and gas ($T_{2G}$ 220 and $T_{1GB}$ 225) are shown, as is the dead-oil curve 230 (corresponding to oil with a gas-oil ratio of zero). R values corresponding to R=1 (232), R=2 (233), R=5 (234), R=10 (235), R=20 (236), R=50 (237), and R=100 (238) are also shown as a series of diagonal lines crossing the volumetric porosity solution space 206. Several constraints, determined mainly by the physical characteristics of water and oil, can each be used to limit the size of the $T_1$-$T_2$ space to the boundary 200, including:

- Since $R \geq 1$ at boundary 240 (because $T_1$ is not less than $T_2$), it is easy to see that the lower-half of the space 206 is infeasible.
- Due to the physical realities of surface relaxation for small pore sizes, it can be safely assumed that irreducible water has $R \leq 5$ at boundary 250.
- At the expected $T_2$ value for gas ($T_{2G}$) along boundary 260, $R \leq 50$ since water, gas, and oil can be present.
- As $T_2$ increases further, lighter and lighter oil can be present and $R \leq 50$ along boundary 270 is proper (because the R of oil$\leq$R of gas).
- The viscosity of oil is usually not significantly less than that of water, therefore $T_1$ of the oil will not significantly exceed that of water along boundary 280.
- No relevant fluids exhibit a $T_2$ greater than that of free water along boundary 290.

Thus, the feasible boundary 200 includes only a fraction of the original space 206 and solving equation (7) with m=1000, p=7, $n_1$=50, and $n_2$=50 using the above constraints reduces the computational time with a laptop computer to a few seconds. Further limiting the values of $n_1$=30 and $n_2$=30 can reduce the computation time to a fraction of a second.

Turning now to the DSA method, which can often be executed with even greater speed than the 2DFC method, it can be seen from equation (2) that each of the measured echoes in an echo train (e.g., echo train A) can be related to $T_1$ and $T_2$ as follows:

$$y_A(t_i) = \sum_k x_k \cdot (1 - e^{-t_{WA}/T_{1k}}) \cdot e^{-t_{Ai}/T_{2k}}. \quad (16)$$

However, the problem presented by equation (16) with respect to solving for $T_1$ and $T_2$ is non-linear. Hence, some embodiments use time-zero inversion and $T_1$-$T_2$ inversion (both being linear problems), in sequence, to find a solution. It should be noted that this type of time-zero inversion is not used in the 2DFC process.

Thus, a linear problem may be formed by first finding the time-zero echoes for each wait time in a given data set. This corresponds to the following $T_2$ inversion problem:

$$\begin{bmatrix} y_A \\ y_B \\ y_C \\ \vdots \end{bmatrix} = \begin{bmatrix} A_A & 0 & 0 & 0 \\ 0 & A_B & 0 & 0 \\ 0 & 0 & A_C & 0 \\ 0 & 0 & 0 & \cdots \end{bmatrix} \begin{bmatrix} x_{T_{2A}} \\ x_{T_{2B}} \\ x_{T_{2C}} \\ \vdots \end{bmatrix} \Leftrightarrow y = Ax, \quad (17)$$

where $A_A = e^{-t_A/T_2} \in \Re^{m_A \times n_2}$, $A_B = e^{-t_B/T_2} \in \Re^{m_B \times n_2}$, $A_C = e^{-t_C/T_2} \in \Re^{m_C \times n_2}$, and $x_{T_{2A}}$, $x_{T_{2B}}$, and $x_{T_{2C}}$ denote the $T_2$ distributions for the three longest wait times. Again, one or more regularization terms may be added to provide the following linear least-squares time-zero inversion:

$$x^* = \arg\min_{x \geq 0} \|Ax - y\|_2^2 + \alpha \|Lx\|_2^2. \quad (18)$$

After having solved the optimization problem (18), the time-zero echo on the $T_1$ buildup curve for each wait time may be obtained by summing the amplitudes in the corresponding $T_2$ distribution $x_{T_{2A}}$, $x_{T_{2B}}$ and $x_{T_{2C}}$, etc. The advantage of including all wait times in the same problem is that constraints on the relationships between $T_2$ distributions for different wait times can be utilized when solving Eq. (18). For instance, for each transverse relaxation time, the porosity should be monotonically decreasing with wait time. When the time-zero echoes have been found, the simultaneous $T_1T_2$-inversion can be formed.

Denoting the vector of time-zero echoes by $m \in \Re^{n_w \times 1}$, and the $T_1$ polarization matrix by $P = 1 - e^{t_W T_1}$, the simultaneous $T_1T_2$-inversion problem can then be formed as:

$$\begin{bmatrix} m \\ y_A \\ y_B \\ y_C \\ \vdots \end{bmatrix} = \begin{bmatrix} P & 0 & 0 & 0 & 0 \\ 0 & A_A & 0 & 0 & 0 \\ 0 & 0 & A_B & 0 & 0 \\ 0 & 0 & 0 & A_C & 0 \\ 0 & 0 & 0 & 0 & \cdots \end{bmatrix} \begin{bmatrix} x_{T_1} \\ x_{T_{2A}} \\ x_{T_{2B}} \\ x_{T_{2C}} \\ \vdots \end{bmatrix} \Leftrightarrow z = Hx, \quad (19)$$

Note that the $T_2$ distribution $x_{T_{2A}}$ in Eqn. (19) corresponds to the true $T_2$ distribution only if the longest wait time is fully polarized; otherwise the determined $T_2$ distribution is only approximate. Adding $T_1$ and $T_2$ regularization terms results in the following linear least-squares problem:

$$x^* = \arg\min_{x \geq 0} \|Hx - z\|_2^2 + \alpha_{T_1} \|L_{T_1} x\|_2^2 + \alpha_{T_2} \|L_{T_2} x\|_2^2. \quad (20)$$

Thus, it is easy to see that including all wait times and both relaxation distributions in the same problem permits constraints on the relationships between the $T_2$ distributions for different wait times, as well as between the two relaxation distributions, to be utilized. Some of the most useful constraints are those on total porosity between the $T_1$ and $T_2$ distributions, as well as those on the $T_1T_2$ ratio R.

FIGS. 3A and 3B illustrate separate and cumulative $T_1$ and $T_2$ distributions, respectively, according to various embodiments of the invention. In FIG. 3A, the separate distributions of the $T_1$ relaxation times 310 and $T_2$ relaxation times 320 can be seen. In FIG. 3B, the cumulative sums of the $T_1$ relaxation times 330 and $T_2$ relaxation times 340 derived from FIG. 3A are shown. The constraint $R \geq 1$ corresponds to $T_1 \geq T_2$, which means that the longitudinal relaxation time at a particular cumulative amplitude is greater than, or equal to, the transverse relaxation time. In FIG. 3B, the reader can see that this constraint is fulfilled for all cumulative amplitudes by noting that the amplitude of the summed $T_2$ relaxation time 340 curve is at or above the amplitude of the summed $T_1$ relaxation time 330 curve. Constraints such as $R \leq R_{max}$ can be implemented in a similar manner. For example, at a cumulative amplitude of 3.3 in FIG. 3B, the $T_2$ relaxation time is 35 milliseconds and the $T_1$ relaxation time is 1200 milliseconds, corresponding to a ratio R of about 34. Note that R increases with increased horizontal separation between the two curves.

Figure 4:
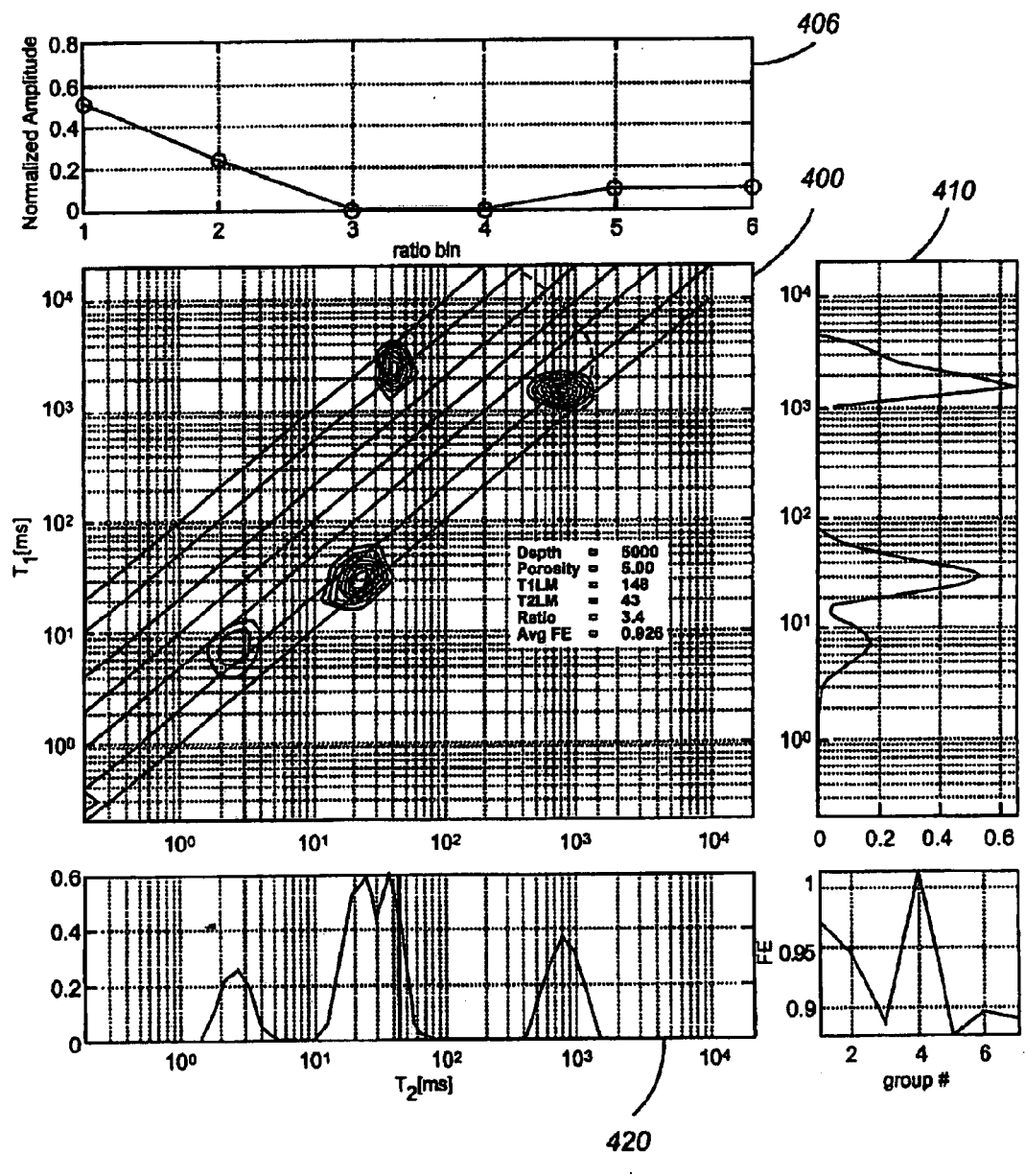
FIG. 4 illustrates an image of porosity distribution, according to various embodiments of the invention.

FIG. 4 illustrates an image of porosity distribution 400, according to various embodiments of the invention. A graph of the normalized sum of the ratio distributions over all relaxation times 406, binned according to groups (e.g., group 1 includes ratios 1-5, group 2 includes ratios 5-10, etc.) is also shown. Whereas solving equation (7) according to the 2DFC method can provide this type of porosity distribution 400 image, solving equation (20) according to the DSA method only provides projections of the image on the $T_1$ and $T_2$ axes (e.g., as $T_1$ projection 410 and $T_2$ projection 420), corresponding to the $T_1$ and $T_2$ distributions. These projections 410, 420 (see also FIG. 3A) provide less information than the image of porosity distribution 400.

For example, using the image of porosity distribution 400, one can, at each relaxation time, relate porosity vs. the ratio R, facilitating improved fluid characterization. Using the $T_1$ and $T_2$ distributions 410, 420 alone, as provided by the DSA method, one does not at each relaxation time know the distribution of porosity vs. R, but rather only the porosity weighted average value of R.

Figure 5:
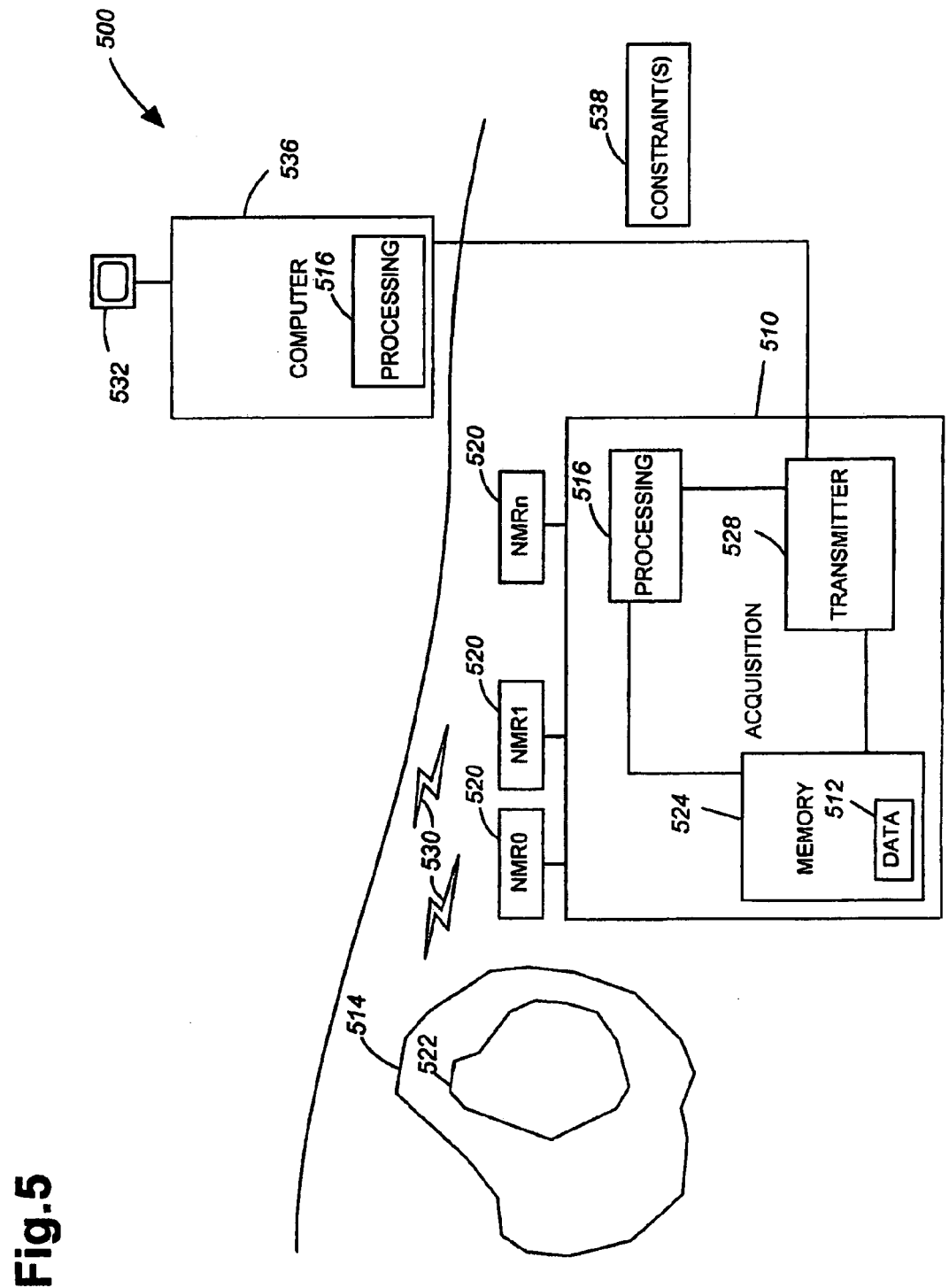
FIG. 5 illustrates an apparatus according to various embodiments of the invention.

A variety of apparatus, systems, and methods may be used to implement the activities described above. For example, FIG. 5 illustrates an apparatus 500 according to various embodiments of the invention.

In some embodiments, the apparatus 500 may include acquisition logic 510 to acquire fluid signature data 512 representing a plurality of NMR echo trains associated with fluids 522 in a material 514, such as a geologic formation. The acquisition logic 510 may thus include one or more acquisition circuits, such as data acquisition circuits that are well known to those of ordinary skill in the art. In addition, the apparatus 500 may include one or more NMR sensors 520 to receive signals 530 associated with the fluid signature data 512, and one or more memories 524 to store the fluid signature data 512.

The apparatus 500 may also include processing logic 516 to provide inverted results by simultaneously inverting a plurality of relaxation time models associated with the fluids 522 using the fluid signature data 512 after constraining ratios of $T_1$ relaxation times to $T_2$ relaxation times. The processing logic 516 may include one or more processing circuits, such as single and multi-core processors that are well known to those of ordinary skill in the art. Thus, the processing logic 516 may operate to receive one or more constraints 538 on one or more ratios of $T_1$ relaxation times to $T_2$ relaxation times. In some cases, the processing logic 516 may operate using an assumption that the fluids 522 are fully-polarized. In other cases, the processing logic 516 may operate using an assumption that the fluids are not fully-polarized.

As described above, the processing logic 516 may operate to provide a two-dimensional volumetric porosity space solution using relaxation time models and fluid signature data 512. In some embodiments, the apparatus 500 may include one or more displays 532 to display visual representations of the two-dimensional volumetric porosity space solution, perhaps in a form similar to or identical to that of FIG. 4.

The processing logic 516 may also be used to determine one or more fluid properties using the inverted results. The display 532 may be used to display the location of a fluid type (e.g., water, gas, and/or oil) based on the determined fluid properties.

Since the processing logic 516 may be located below the surface 526, or above, in some embodiments, the apparatus 500 may include one or more telemetry transmitters 528 to transmit the fluid signature data to an above-ground computer 536, perhaps located at a wellbore surface, or at some remote location (not shown). Thus, the processing logic 516 may be included in a downhole tool, or above-ground (e.g., as part of an above-ground computer workstation, perhaps located in a logging facility), or both.

Figure 6A:
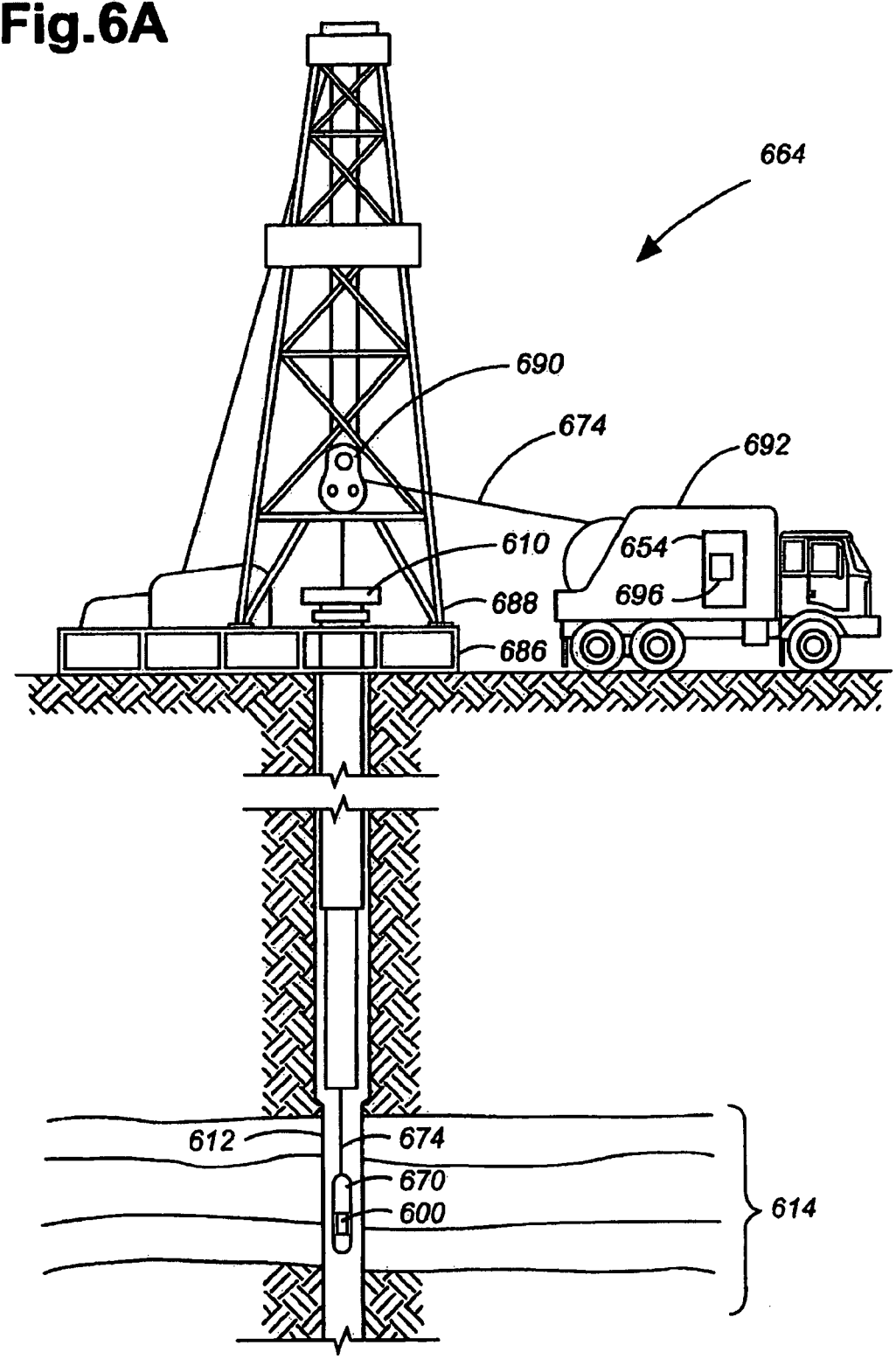
FIGS. 6A-6B illustrate apparatus and systems according to various embodiments of the invention.
Figure 6B:
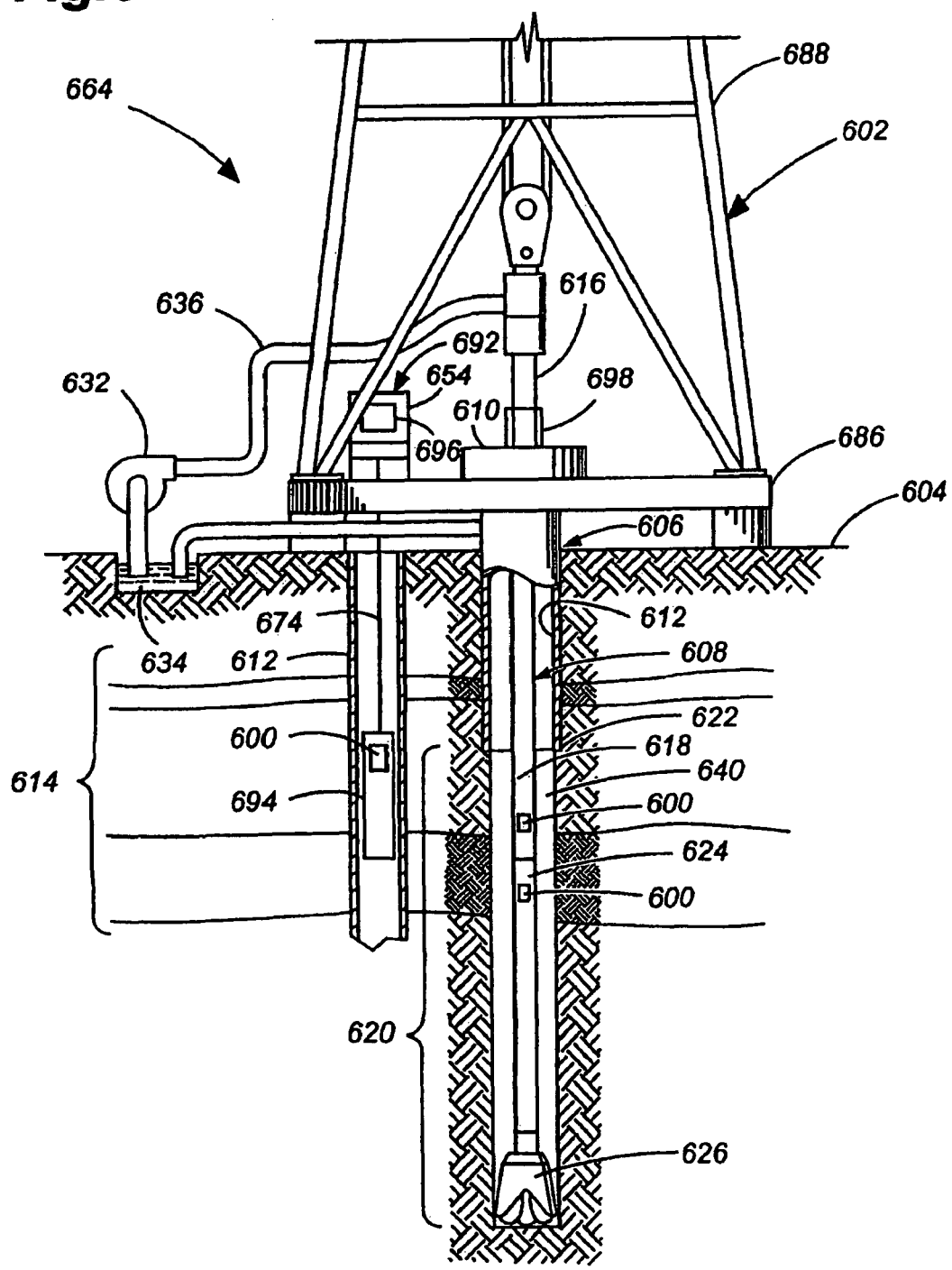

FIGS. 6A-6B illustrate apparatus 600 and systems 664 according to various embodiments of the invention. The apparatus 600, which may be similar to or identical to the apparatus 500 described above and shown in FIG. 5, may comprise portions of a tool body 670 as part of a wireline logging operation, or of a downhole tool 624 as part of a downhole drilling operation. For example, FIG. 6A shows a well during wireline logging operations.

A drilling platform 686 may be equipped with a derrick 688 that supports a hoist 690. Oil and gas well drilling operations are commonly carried out using a string of drill pipes connected together so as to form a drilling string that is lowered through a rotary table 610 into a wellbore or borehole 612.

Here it is assumed that the drilling string has been temporarily removed from the borehole 612 to allow a tool body 670 (e.g., a wireline logging tool), such as a probe or sonde, to be lowered by wireline or logging cable 674 into the borehole 612. Typically, the tool body 670 is lowered to the bottom of the region of interest and subsequently pulled upward at a substantially constant speed. During the upward trip, instruments included in the tool body 670 (e.g., apparatus 600) may be used to perform measurements on the subsurface formations 614 adjacent the borehole 612 as they pass by, or as the tool body 670 remains stationary.

Measurement data (e.g., similar or identical to data 512 of FIG. 5) may include NMR echo train data that can be communicated to a logging facility 692 for storage, processing, and analysis. The logging facility 692 may be provided with electronic equipment for various types of signal processing. Similar log data may be gathered and analyzed during drilling operations (e.g., during logging while drilling (LWD) operations). For example, the tool body 670 in this case may house one or more apparatus 600, and the logging facility 692 may include one or more surface computers 654, similar to or identical to the computer 536 described above with respect to FIG. 5.

Turning now to FIG. 6B, it can be seen how a system 664 may also form a portion of a drilling rig 602 located at a surface 604 of a well 606. The drilling rig 602 may provide support for a drill string 608. The drill string 608 may operate to penetrate a rotary table 610 for drilling a borehole 612 through subsurface formations 614. The drill string 608 may include a Kelly 616, drill pipe 618, and a bottom hole assembly 620, perhaps located at the lower portion of the drill pipe 618. The drill string 608 may include wired and unwired drill pipe, as well as wired and unwired coiled tubing, including segmented drilling pipe, casing, and coiled tubing.

The bottom hole assembly 620 may include drill collars 622, a downhole tool 624, and a drill bit 626. The drill bit 626 may operate to create a borehole 612 by penetrating the surface 604 and subsurface formations 614. The downhole tool 624 may comprise any of a number of different types of tools including measurement while drilling (MWD) tools, LWD tools, and others.

During drilling operations, the drill string 608 (perhaps including the Kelly 616, the drill pipe 618, and the bottom hole assembly 620) may be rotated by the rotary table 610. In addition to, or alternatively, the bottom hole assembly 620 may also be rotated by a motor (e.g., a mud motor) that is located downhole. The drill collars 622 may be used to add weight to the drill bit 626. The drill collars 622 may also stiffen the bottom hole assembly 620 to allow the bottom hole assembly 620 to transfer the added weight to the drill bit 626, and in turn, assist the drill bit 626 in penetrating the surface 604 and subsurface formations 614.

During drilling operations, a mud pump 632 may pump drilling fluid (sometimes known by those of ordinary skill in the art as "drilling mud") from a mud pit 634 through a hose 636 into the drill pipe 618 and down to the drill bit 626. The drilling fluid can flow out from the drill bit 626 and be returned to the surface 604 through an annular area 640 between the drill pipe 618 and the sides of the borehole 612. The drilling fluid may then be returned to the mud pit 634, where such fluid is filtered. In some embodiments, the drilling fluid can be used to cool the drill bit 626, as well as to provide lubrication for the drill bit 626 during drilling operations. Additionally, the drilling fluid may be used to remove subsurface formation 614 cuttings created by operating the drill bit 626.

Thus, referring now to FIGS. 5 and 6A-6B, it may be seen that in some embodiments, the system 664 may include a drill collar 622, and/or a downhole tool 624, including a tool body 670 or a substantially permanently installed probe 694 (in a downhole well), to which one or more apparatus 600 are attached. Thus, the processing logic 516 (see FIG. 5) may be included in the downhole tool 624, or in a surface computer (e.g., computer 654).

The downhole tool 624 may comprise an LWD tool or MWD tool. The tool body 670 may comprise a wireline logging tool, including a probe or sonde, for example, coupled to a cable 674, such as a wireline or logging cable. Thus, a wireline 674 or a drill string 608 may be mechanically coupled to the downhole tool 624. In some embodiments, the system 664 may include a steering mechanism 698 to steer the drill bit 626 into a selected geological zone or subsurface formation 614 responsive to the determined properties of the fluids.

In some embodiments, the system 664 may include one or more displays 696 to display visual representations of the fluid properties and a variety of fluid characteristics such as a porosity distribution image. The display 696 may be included as part of a surface computer 654 used to receive data from the acquisition logic 510 (see FIG. 5), if desired.

The buildup curve 110; data sequence 116; echo trains 120; feasible boundary 200; porosity solution space 206; $T_{2W}$ 210; $T_{1WB}$ 215; $T_{2G}$ 220; $T_{1GB}$ 225; dead-oil curve 230; R values 232, 233, 234, 235, 236, 237, 238; boundaries 240, 250, 260, 270, 280, 290; distributions 310, 320; cumulative sums 330, 340; porosity distribution 400; graph 406; projections 410, 420; apparatus 500, 600; acquisition logic 510; fluid signature data 512; material 514; processing logic 516; NMR sensors 520; fluids 522; memories 524; surfaces 526, 604; transmitters 528; signals 530; displays 532, 696; computers 536, 654; constraints 538; drilling rig 602; well 606; drill string 608; rotary table 610; borehole 612; formations 614; Kelly 616; drill pipe 618; bottom hole assembly 620; drill collars 622; downhole tool 624; drill bit 626; mud pump 632; mud pit 634; hose 636; annular area 640; tool body 670; logging cable 674; drilling platform 686; derrick 688; hoist 690; logging facility 692; probe 694; and steering mechanism 698 may all be characterized as "modules" herein. Such modules may include hardware circuitry, and/or a processor and/or memory circuits, software program modules and objects, and/or firmware, and combinations thereof, as desired by the architect of the apparatus 500, 600 and systems 664, and as appropriate for particular implementations of various embodiments. For example, in some embodiments, such modules may be included in an apparatus and/or system operation simulation package, such as a software electrical signal simulation package, a power usage and distribution simulation package, a power/heat dissipation simulation package, and/or a combination of software and hardware used to simulate the operation of various potential embodiments.

It should also be understood that the apparatus and systems of various embodiments can be used in applications other than for drilling and logging operations, and thus, various embodiments are not to be so limited. The illustrations of apparatus 500, 600 and systems 664 are intended to provide a general understanding of the structure of various embodiments, and they are not intended to serve as a complete description of all the elements and features of apparatus and systems that might make use of the structures described herein.

Applications that may include the novel apparatus and systems of various embodiments include electronic circuitry used in high-speed computers, communication and signal processing circuitry, modems, processor modules, embedded processors, data switches, and application-specific modules, including multilayer, multi-chip modules. Such apparatus and systems may further be included as sub-components within a variety of electronic systems, such as process measurement instruments, personal computers, workstations, and vehicles, among others. Some embodiments include a number of methods.

Figure 7:
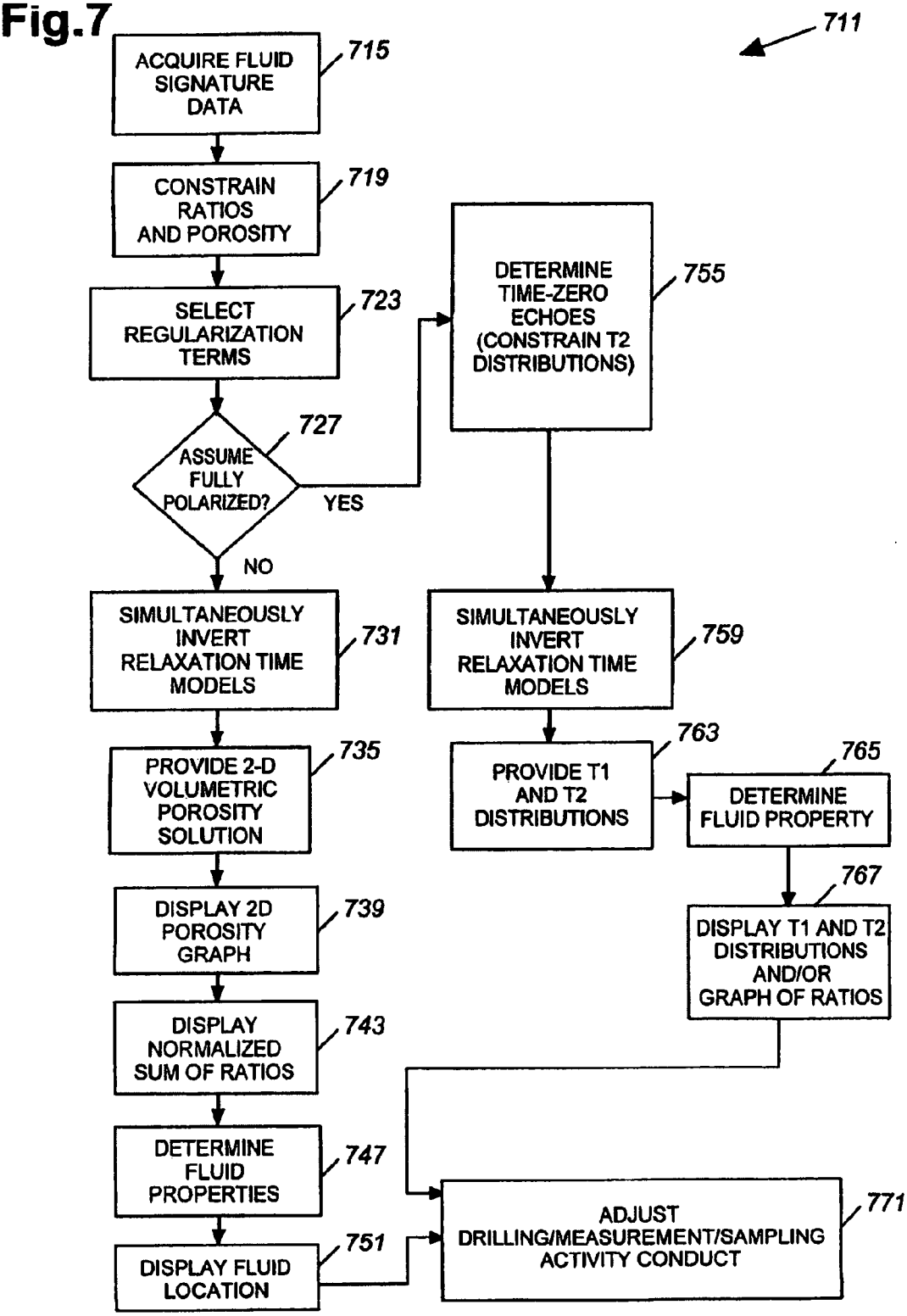
FIG. 7 illustrates a method flow diagram according to various embodiments of the invention.

For example, FIG. 7 illustrates a method flow diagram 711 according to various embodiments of the invention. In some embodiments, a method 711, such as a method of simultaneously inverting $T_1$ and $T_2$ spectra to determine properties of fluids in a material, may begin at block 715 with acquiring fluid signature data representing a plurality of NMR echo trains associated with fluids in a material. The method 711 may include, at block 719, constraining one or more ratios of $T_1$ relaxation times to $T_2$ relaxation times to be between a minimum of 1 and a maximum derived from properties of potential reservoir fluids (e.g., water, gas, and/or oil), a magnetic field tool gradient G, and inter-echo spacing $t_E$ used to acquire the fluid signature data. Porosity may also be constrained. The method 711 may also include, at block 723, selecting regularization terms, perhaps to determine solution smoothness of a two-dimensional volumetric porosity space solution (e.g., in the 2DFC method) prior to solving a linear least-squares problem.

In some embodiments, the method 711 operates with the assumption that the fluids are fully-polarized. In others, the method 711 operates under the assumption that the fluids are not fully-polarized. Thus, at block 727, a determination is made as to which assumption is operative.

If the fluids are not assumed to be fully polarized at block 727, the method 711 may continue with simultaneously inverting a plurality of relaxation time models that do not operate on an assumption that the fluids are fully-polarized to provide inverted results at block 731. As noted above, the relaxation time models may be associated with the fluids using the fluid signature data after constraining ratios of $T_1$ relaxation times to $T_2$ relaxation times. Simultaneous inversion in some cases may include selecting one or more regularization terms to determine a solution smoothness prior to solving a linear least-squares problem.

In some embodiments, the method 711 may include providing a two-dimensional volumetric porosity space solution using the relaxation time models and the fluid signature data at block 735.

In some embodiments, the method 711 at block 739 may include displaying a two-dimensional graph of porosity associated with the fluids versus the ratios of $T_1$ relaxation times to $T_2$ relaxation times. The method 711 may include displaying a normalized sum of the ratios over all of the $T_1$ relaxation times and the $T_2$ relaxation times at block 743.

In some embodiments, the method 711 may include determining a property of the fluid using the inverted results at block 747. A fluid type, including gas, oil, and/or water, may be determined based on the determined fluid property or properties, perhaps comprising a relative viscosity and/or a relative diffusivity.

Thus, the method 711 may include displaying the location of a fluid type based on the determined properties at block 751 (see FIG. 4, for example). The method 711 may also include adjusting conduct of a drilling, measurement, or sampling activity based on one or more fluid properties in substantially real time at block 771. For example, the drilling direction may be changed, selected formation properties may be measured, and/or selected samples may be taken at a particular location.

If the fluids are assumed to be fully polarized at block 727, the method 711 may continue with determining a single time-zero echo for each wait time included in the nuclear magnetic resonance echo trains to provide a plurality of time-zero echoes at block 755. The method 711 may include constraining the plurality of time-zero echoes to be monotonically increasing with increasing wait time. For example, determining a single time-zero echo for each wait time included in the nuclear magnetic resonance echo trains to provide a plurality of time-zero echoes may include constraining the distributions of $T_2$ relaxation times to have a monotonically increasing amplitude at each $T_2$ relaxation time within the distributions of $T_2$ relaxation times, with increasing wait time.

The method 711 may continue with simultaneously inverting a plurality of relaxation time models that operate on an assumption that the fluids are fully-polarized at block 759. Again, the models may be associated with the fluid to provide distributions of $T_1$ relaxation times and distributions of $T_2$ relaxation times based on the plurality of time-zero echoes and the fluid signature data after constraining ratios of the $T_1$ relaxation times to the $T_2$ relaxation times. In addition, simultaneous inversion may in some cases include selecting one or more regularization terms to determine a solution smoothness prior to solving a linear least-squares problem.

In some embodiments, the method 711 may include providing distributions of $T_1$ relaxation times and distributions of $T_2$ relaxation times using the plurality of time-zero echoes and the fluid signature data at block 763. One or more properties of the fluids in the material (e.g., geologic formation) may be determined using the distributions at block 765. Again, a fluid type, including gas, oil, and/or water, may be determined based on the determined fluid property or properties, perhaps comprising a relative viscosity and/or a relative diffusivity. The method 711 may also include displaying $T_1$ and $T_2$ distributions, as well as a graph of the porosity-weighted average value of the ratios versus the $T_2$ relaxation times at block 767. The method 711 may continue on to block 771, described previously.

It should be noted that the methods described herein do not have to be executed in the order described, or in any particular order. Moreover, various activities described with respect to the methods identified herein can be executed in iterative, serial, or parallel fashion. Information, including parameters, commands, operands, and other data, can be sent and received, and perhaps stored using a variety of media, tangible and intangible, including one or more carrier waves.

Upon reading and comprehending the content of this disclosure, one of ordinary skill in the art will understand the manner in which a software program can be launched from a computer-readable medium in a computer-based system to execute the functions defined in the software program. One of ordinary skill in the art will further understand that various programming languages may be employed to create one or more software programs designed to implement and perform the methods disclosed herein. The programs may be structured in an object-orientated format using an object-oriented language such as Java or C++. Alternatively, the programs can be structured in a procedure-orientated format using a procedural language, such as assembly or C. The software components may communicate using any of a number of mechanisms well known to those skilled in the art, such as application program interfaces or interprocess communication techniques, including remote procedure calls. The teachings of various embodiments are not limited to any particular programming language or environment. Thus, other embodiments may be realized.

FIG. 8 is a block diagram of an article of manufacture, or article 885 according to various embodiments, such as a computer, a memory system, a magnetic or optical disk, some other storage device, and/or any type of electronic device or system. The article 885 may include a processor 887 coupled to a computer-readable medium 889 such as a memory (e.g., fixed and removable storage media, including tangible memory having electrical, optical, or electromagnetic conductors; or even intangible memory, such as a carrier wave) having associated information 891 (e.g., computer program instructions and/or data), which when executed by a computer, causes the computer 887 (e.g., a microprocessor or workstation) to perform a method including such actions as acquiring fluid signature data representing a plurality of nuclear magnetic resonance echo trains associated with fluids in a material, simultaneously inverting a plurality of relaxation time models to provide inverted results (wherein the relaxation time models are associated with the fluids using the fluid signature data after constraining ratios of $T_1$ relaxation times to the $T_2$ relaxation times), and determining a property of the fluid using the inverted results.

Additional actions may include Operating under an assumption that the fluids are (or are not) fully-polarized, determining a single time-zero echo for each wait time included in the nuclear magnetic resonance echo trains to provide a plurality of time-zero echoes, inverting the relaxation time models, and providing distributions of $T_1$ relaxation times and distributions of $T_2$ relaxation times using the plurality of time-zero echoes and the fluid signature data.

In some embodiments, such actions may include providing a two-dimensional volumetric porosity space solution using the relaxation time models and the fluid signature data, and adjusting conduct of a drilling activity based on the determined property in substantially real time.

Implementing the apparatus, systems, and methods of various embodiments may permit obtaining $T_1$ and $T_2$ distributions that satisfy R ratio constraints using data from a single logging pass, such that the total porosity in $T_1$ and $T_2$ distributions are substantially equal. Results may also include obtaining more accurate distributions compared to existing inversion methods.

Specific benefits of the DSA method may include a faster computation speed. Specific benefits derived from implementing the 2DFC method may include the provision of a two-dimensional volumetric map of porosity, and distributions of porosity versus the ratio R for each relaxation time. More accurate distributions compared to the DSA method may also be available.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. An apparatus, comprising:
   acquisition logic to acquire fluid signature data representing a plurality of nuclear magnetic resonance echo trains associated with fluids in a material; and
   processing logic to provide inverted results by simultaneously inverting a plurality of relaxation time models associated with the fluids using the fluid signature data after constraining ratios of $T_1$ relaxation times to $T_2$ relaxation times, and to determine a property of the fluid using the inverted results.

2. The apparatus of claim 1, wherein the processing logic operates under an assumption that the fluids are fully-polarized.

3. The apparatus of claim 1, wherein the processing logic does not operate under an assumption that the fluids are fully-polarized.

4. The apparatus of claim 1, wherein the processing logic provides a two-dimensional volumetric porosity space solution using relaxation time models and the fluid signature data.

5. The apparatus of claim 4, comprising:
   a display to display visual representations of the two-dimensional volumetric porosity space solution.

6. The apparatus of claim 1, comprising:
   NMR sensors to receive signals associated with the fluid signature data.

7. The apparatus of claim 1, comprising:
   a memory to store the fluid signature data.

8. The apparatus of claim 1, wherein the processing logic is to receive at least one constraint on at least one of the ratios of $T_1$ relaxation times to $T_2$ relaxation times.

9. The apparatus of claim 1, comprising:
   a telemetry transmitter to transmit the fluid signature data to an above-ground computer at any one of a wellbore surface and a remote location.

10. The apparatus of claim 1, comprising:
    a display to display a location of a fluid type based on the property.

11. The apparatus of claim 1, wherein the acquisition logic comprises an acquisition circuit, and wherein the processing logic comprises a processing circuit.

12. A system, comprising:
    a downhole tool;
    acquisition logic included in the downhole tool to acquire fluid signature data representing a plurality of nuclear magnetic resonance echo trains associated with fluids in a material; and
    processing logic to provide inverted results by simultaneously inverting a plurality of relaxation time models associated with the fluids using the fluid signature data after constraining ratios of $T_1$ relaxation times to $T_2$ relaxation times, and to determine a property of the fluid using the inverted results.

13. The system of claim 12, wherein the processing logic is included in the downhole tool.

14. The system of claim 12, comprising:
    a wireline coupled to the downhole tool.

15. The system of claim 12, comprising:
    a drill bit mechanically coupled to a drill string and the downhole tool; and
    a steering mechanism to steer the drill bit into a selected geological zone responsive to the property.

16. The system of claim 15, wherein the drill string includes at least one of segmented drilling pipe, casing, and coiled tubing.

17. The system of claim 12, wherein the acquisition logic comprises an acquisition circuit, and wherein the processing logic comprises a processing circuit.

18. A method, comprising:
    acquiring fluid signature data representing a plurality of nuclear magnetic resonance echo trains associated with fluids in a material;
    simultaneously inverting a plurality of relaxation time models that do not operate on an assumption that the fluids are fully-polarized, wherein the models are associated with the fluids to provide a two-dimensional volumetric porosity space solution based on the fluid signature data after constraining ratios of $T_1$ relaxation times to $T_2$ relaxation times; and
    determining a property of the fluid using the two-dimensional volumetric porosity space solution.

19. The method of claim 18, comprising:
    constraining at least one of the ratios to be between a minimum of 1 and a maximum derived from properties of potential reservoir fluids, a magnetic field tool gradient, and inter-echo spacing used to acquire the fluid signature data.

20. The method of claim 18, wherein the simultaneously inverting includes:
    selecting regularization terms to determine solution smoothness of the two-dimensional volumetric porosity space solution prior to solving a linear least-squares problem.

21. The method of claim 18, comprising:
displaying a graph of porosity associated with the fluids versus the ratios of $T_1$ relaxation times to $T_2$ relaxation times.

22. The method of claim 18, comprising:
displaying a normalized sum of the ratios over all of the $T_1$ relaxation times and the $T_2$ relaxation times.

23. The method of claim 18, comprising:
displaying a location of a fluid type based on the property.

24. The method of claim 18, comprising:
based on the property, determining a fluid type to include at least one of a gas, an oil, and water.

25. The method of claim 18, wherein the property comprises one of a relative viscosity and a relative diffusivity.

26. A method, comprising:
acquiring fluid signature data representing a plurality of nuclear magnetic resonance echo trains associated with fluids in a material;
determining a single time-zero echo for each wait time included in the nuclear magnetic resonance echo trains to provide a plurality of time-zero echoes;
simultaneously inverting a plurality of relaxation time models that operate on an assumption that the fluids are fully-polarized, wherein the models are associated with the fluid to provide distributions of $T_1$ relaxation times and distributions of $T_2$ relaxation times based on the plurality of time-zero echoes and the fluid signature data after constraining ratios of the $T_1$ relaxation times to the $T_2$ relaxation times; and
determining a property of the fluid using the distributions.

27. The method of claim 26, comprising:
constraining at least one of the ratios between a minimum of 1 and a maximum derived from properties of potential reservoir fluids, a magnetic field tool gradient, and inter-echo spacing used to acquire the fluid signature data.

28. The method of claim 26, wherein the simultaneously inverting includes:
selecting at least two regularization terms to determine a solution smoothness prior to solving a linear least-squares problem.

29. The method of claim 26, comprising:
displaying a graph of a porosity-weighted average value of the ratios versus the $T_2$ relaxation times.

30. The method of claim 26, comprising:
constraining the plurality of time-zero echoes to be monotonically increasing with increasing wait time.

31. The method of claim 26, determining a single time-zero echo for each wait time included in the nuclear magnetic resonance echo trains to provide a plurality of time-zero echoes includes:
constraining the distributions of $T_2$ relaxation times to have a monotonically increasing amplitude at each $T_2$ relaxation time within the distributions of $T_2$ relaxation times, with increasing wait time.

32. The method of claim 26, comprising:
based on the property, determining a fluid type to include at least one of a gas, an oil, and water.

33. The method of claim 26, wherein the property comprises one of a relative viscosity and a relative diffusivity.

34. A computer-readable medium having instructions stored thereon which, when executed by a computer, cause the computer to perform a method comprising:
acquiring fluid signature data representing a plurality of nuclear magnetic resonance echo trains associated with fluids in a material;
simultaneously inverting a plurality of relaxation time models to provide inverted results, wherein the relaxation time models are associated with the fluids using the fluid signature data after constraining ratios of $T_1$ relaxation times to $T_2$ relaxation times; and
determining a property of the fluid using the inverted results.

35. The computer-readable medium of claim 34, wherein the instructions, when executed by the computer, cause the computer to perform a method comprising:
operating under an assumption that the fluids are fully-polarized.

36. The computer-readable medium of claim 34, wherein the instructions, when executed by the computer, cause the computer to perform a method comprising:
determining a single time-zero echo for each wait time included in the nuclear magnetic resonance echo trains to provide a plurality of time-zero echoes.

37. The computer-readable medium of claim 36, wherein the instructions, when executed by the computer, cause the computer to perform a method comprising:
inverting the relaxation time models; and
providing distributions of $T_1$ relaxation times and distributions of $T_2$ relaxation times using the plurality of time-zero echoes and the fluid signature data.

38. The computer-readable medium of claim 34, wherein the instructions, when executed by the computer, cause the computer to perform a method comprising:
operating under an assumption that the fluids are not fully-polarized.

39. The computer-readable medium of claim 38, wherein the instructions, when executed by the computer, cause the computer to perform a method comprising:
providing a two-dimensional volumetric porosity space solution using the relaxation time models and the fluid signature data.

40. The computer-readable medium of claim 34, wherein the instructions, when executed by the computer, cause the computer to perform a method comprising:
adjusting conduct of a drilling, measurement, or fluid sampling activity based on the property in substantially real time.

41. The computer-readable medium of claim 34, wherein the instructions, when executed by the computer, cause the computer to perform a method comprising:
determining a drilling direction, based on the property, to drill into a geological zone comprising at least one of a hydrocarbon zone, a permeable zone, or a non-shale zone.

* * * * *

UNITED STATES PATENT AND TRADEMARK OFFICE
CERTIFICATE OF CORRECTION

PATENT NO. : 8,395,384 B2  
APPLICATION NO. : 12/519956  
DATED : March 12, 2013  
INVENTOR(S) : Fransson et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 905 days.

Signed and Sealed this  
First Day of September, 2015

Michelle K. Lee  
*Director of the United States Patent and Trademark Office*